(12) United States Patent
Diaz et al.

(10) Patent No.: US 7,087,402 B2
(45) Date of Patent: Aug. 8, 2006

(54) SELECTIVE TRANSESTERIFICATION OF STANOLS IN MIXTURES COMPRISING STEROLS AND STANOLS

(75) Inventors: Miguel Angel Fuenzalida Diaz, Santiago (CL); Alejandro Markovits Rojas, Santiago (CL); Endre Markovits Schersl, Santiago (CL); Irene Martinez Basterrechea, Santiago (CL)

(73) Assignee: Harting, S.A., Santiago (CL)

( * ) Notice: Subject to any disclaimer, the term of this patent is extended or adjusted under 35 U.S.C. 154(b) by 311 days.

(21) Appl. No.: 10/205,957

(22) Filed: Jul. 26, 2002

(65) Prior Publication Data

US 2003/0100044 A1    May 29, 2003

(30) Foreign Application Priority Data

Aug. 22, 2001 (CL) ................................. 2045-2001

(51) Int. Cl.
*C12P 33/00* (2006.01)
*C12P 7/64* (2006.01)

(52) U.S. Cl. ........................................ 435/52; 435/134
(58) Field of Classification Search ................... 435/52
See application file for complete search history.

(56) References Cited

U.S. PATENT DOCUMENTS 6,660,491 B1 * 12/2003 Norinobu et al. ............. 435/19

OTHER PUBLICATIONS

Weber et al., "Fatty Acid Steryl, Stanyl, and Steriod Esters by Esterification and Transesterification in Vacuo Using *Candida rugosa* Lipase as Catalyst", J. Agric. Food Chem. 2001, 49:67-71 (Nov. 8, 2000).*

King et al., "Sterol ester production using lipase-catalyzed reactions in supercritical carbon dioxide", Eur. Food Res. Technol. (2001) 212:566-569 (Mar. 29, 2001).*

* cited by examiner

*Primary Examiner*—Sandra E. Saucier
(74) *Attorney, Agent, or Firm*—Baker & McKenzie LLP

(57) ABSTRACT

The present invention is related to a process for selectively transesterifying stanols in mixtures comprising sterols and stanols, and a process for separating sterols from said mixtures.

The process of selective transesterification comprises the forming of a reacting mixture by contacting a selective lipase with a reactant mixture comprising sterols and stanols and an ester selected from the group consisting of esters of an organic acid with a short chain aliphatic alcohol. The transetrifying is carried out agitated reactors at pressures below atmospheric pressure and temperatures from 30 to 90° C.

The process for separating a fraction comprising sterols from a mixture comprising sterols and stanols comprises the steps:
  a) forming a reactive mixture by contacting a selective lipase with a reactant mixture comprising sterols and stanols and an ester selected from the group consisting of esters of an organic acid with a short chain aliphatic alcohol;
  b) forming a reacted mixture by separating the selective lipase from the reacting; and
  c) separating from the reacted mixture a fraction comprising sterols The reaction is carried out in agitated reactors at pressures below atmospheric pressure and temperatures from 30 to 90° C.

Recovering from the reacted mixture of a fraction comprising sterols comprise one or more distillation steps at reduced pressure or one or more distillation and crystallization steps.

10 Claims, 1 Drawing Sheet

SELECTIVE TRANSESTERIFICATION OF STANOLS IN MIXTURES COMPRISING STEROLS AND STANOLS

BACKGROUND AND SUMMARY OF THE INVENTION

The present invention relates to a process for the selective transesterification of stanols in mixtures comprising sterols and stanols and a process for separating sterols from mixtures containing sterols and stanols.

Steroids, either from plants (phytosteroids) or animals (zoosteroids) are chemical compounds whose molecules present a perhydrocyclopentanophenantrene nucleus and some of them also have a hydrocarbon chain joined to carbon 17 of this nucleus.

Among steroids are the steroid alcohols which present at least one hydroxile group joined to carbon C-3 of the nucleus. In the present invention, the term "sterol" stands for a steroid alcohol comprising a double bond in carbon C-5 of the nucleus. Likewise the term "stanol" stands for a steroid alcohol lacking a double bond in carbon C-5 of the nucleus. Sterols and stanols commonly known in the state of art are included among sterols or stanols of the present invention.

Significant amounts of steroid alcohols can be found in the residue of the degumming of edible oils such as soy bean oil, sunflower oil, maize germ oil, palm oil, rapeseed oil or in the so called wood alcohols derived from black liquor soaps from Kraft cellulose pulping process, or from tall oil, or from the residue of tall oil distillation known as tall oil pitch.

Most steroid alcohols from plants, or phytosterols, which include wood alcohols as well, usually contain both sterols and stanols.

Processes for the recovery and purification of phytosterols are well known in the art. Table I below shows a typical composition of wood alcohols from black liquor soaps.

TABLE I

Typical composition of wood alcohols from black liquor soaps.

| Steroid alcohol | Percentage in weight |
| --- | --- |
| Beta-sitosterol | 68 |
| Beta-sitostanol | 20 |
| Campesterol | 7 |
| Campestanol | 2 |
| Stigmasterol | <1 |

Mixtures of steroid alcohols ocasionally contain steryl or stanyl esters besides free steroid alcohols. To utilize the process of separation herein disclosed in these cases, the mixtures have to be first hydrolyzed, either by enzymatic hydrolysis or alkaline saponification, and the resulting unsaponifiable material comprising sterols and stanols once recovered from the hydrolized or saponified mixture, may be subjected to the fractionation process of the present invention. The process herein disclosed can be used with mixtures of steroid alcohols of either plant or animal origin and also with any unsaponifiable mixture comprising sterols and stanols.

Both sterols and stanols have important commercial applications. Sterols, mainly beta-sitosterol, can be transformed by fermentation into useful intermediaries for the synthesis of steroid drugs. Stanols are less suitable for microbial transformation, therefore it might be advisable to remove them from the mixture of steroid alcohols prior to fermentation. On the other hand, stanols esterified with organic acids, in general fatty acids, or stanyl esters of fatty acids, are efficient blod cholesterol lowering agents and as such are in high demand as nutraceutical ingredients for food products.

Therefore it might be convenient to separate sterols from stanols in mixtures comprising steroid alcohols, in order to obtain pure sterols for the pharmaceutical industry and stanyl esters or stanols for neutraceutical industry. However, no processes for the separation of sterols from stanols are known. Therefore, the pharmaceutical industry has to resort to steroid alcohol mixtures whose fermentation, as explained above is less effcient as that of pure sterols, and the nutraceutical industry for the obtention of stanols or stanol esters has to resort to the transformation of the whole mixture of steroid alcohols into steroid esters. One of such processes is dislosed in U.S. Pat. No. 5,502,045. The process disclosed consists in the catalytic hydrogenation of the mixture of steroid alcohols to reduce sterols to stanols, followed by the chemical transesterification of the mixture using methyl esters of fatty acids in the presence of the catalyst sodium ethylate. Among its disadvantages, hydogenation eliminates the valuable beta-sitosterol, and additionally, the process may lead to the formation of an asymmetric carbon center in C-5, so that enantiomeric mixtures with non-natural configuration isomers and unknown metabolic effects could be generated.

Therefore, it is convenient to separate sterols and stanols from mixtures of steroid alcohols in order to obtain high quality sterols for fermentation or other uses and natural stanols or stanol esters as nutraceutical food ingredients.

However, beta-sitostanol and beta-sitosterol, whose structures are shown below, have practically identical physical and chemical properties turning almost unthinkable any effective technique to separate them. This fact is reflected in the total absence of any reference on the subject in the art.

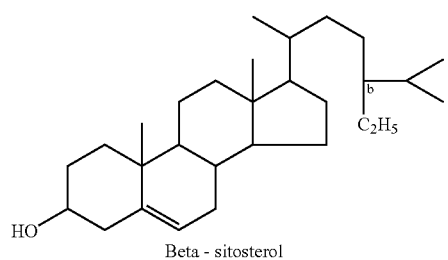
Beta - sitosterol

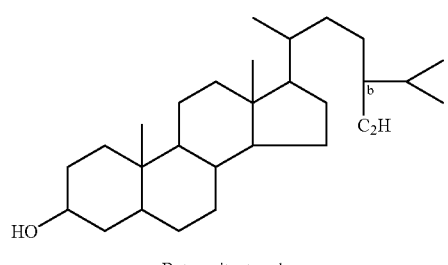
Beta - sitostanol

DETAILED DESCRIPTION OF THE INVENTION

In the present invention, it has been observed that certain microbial lipases, hereafter denoted as selective lipases, surprisingly and unexpectedly exhibit a selective transesterifying action on stanols in a reacting mixture, when a reactant mixture comprising sterols, stanols, and one or more components selected from the group consisting of organic acids esterifyed with short chain aliphatic alcohols, is contacted with such selective lipases, thereby forming a reacting mixture.

Upon separating the selective lipase from the reacting mixture, a reacted mixture is obtained. Given the surprising characteristics of the selective lipase, in the reacted mixture, the conversion as defined below, of stanols to stanyl esters is greater than the conversion of sterols to steryl esters.

The conversion of stanols to stanyl esters ($X_{stanol}$) in a reacted mixture is calculated by means of the expression:

$$X_{stanols} = (C_{0stanols} - C_{stanols})/C_{0stanols}$$

Where:

$C_{0stanols}$ is the concentration of stanols in reactant mixture $C_{stanols}$ is the concentration of stanols in reacted mixture Similarly, conversion of sterols to steryl esters ($X_{sterols}$) is calculated by means of the expression;

$$X_{sterols} = (C_{0sterols} - C_{sterols})/C_{0sterols}$$

Where:

$C_{0sterols}$ is the concentration of sterols in reactant mixture $C_{sterols}$ is the concentration of sterols in reacted mixture Concentrations may be expressed in any unit, preferably as percentage in weight. Selective lipase is any formulation expressing selective lipase activity and may comprise one or more compounds derived from a fermentation broth of a microorganism or one or more compounds derived from a cellular extract of a microorganism. In these cases the formulation is called free selective lipase preparation. Alternatively, the formulation may comprise an inert solid immobilizing one or more compounds derived from a fermentation broth of a microorganism or an inert solid immobilizing one or more compounds derived from a cellular extract of a microorganism. In these cases the formulation is called immobilized selective lipase preparation. Compounds derived from a fermentation broth of bacteria of the genus *Alcaligenes* such as *Alcaligenes* sp or compounds derived from a cellular extract of bacteria of the genus *Alcaligenes* such as *Alcaligenes* sp are suitable for making selective lipase, either free or immobilized.

A lipolytic unit is the amount of formulation that liberates 1 micromole of fatty acid per minute at 37° C. from olive oil emulsified in presence of polyvinyl alcohol. The method for determining lipolytic activity used in the present invention is described in U.S. Pat. No. 5,219,733, being a standard technique for measuring lipolytic activity. It has been observed that there is a correlation between hydrolytic and transesterifying activities of the selective lipases of the present invention.

The reaction can be carried out in presence either of a stoichiometric amount or stoichiometric excess of esters of organic acids.

In the first case, the reacted mixture comprises steroid alcohols and esters of steroid alcohols.

In the second case, the reacted mixture additionally comprises esters of organic acids.

In both cases, the reacted mixture can be used without further processing as food ingredients if wished.

Nevertheless, in most cases it might be desirable to fractionate the mixture separating non-esterifyed sterols from the esterified fraction of the mixture.

There are several processes for separating these fractions from the reacted mixture that can be used either if the reacted mixture comprise esters of organic acids or if it does not comprise them. The reacted mixture can be separated or resolved into different fractions by distillation at low pressure in either a short path distillation column with internal condenser or in a thin film evaporator with fractionation column and external condenser, as described in the examples below. Some of the processes useful for the recovery of sterols from reacted mixtures comprise:

Process 1

The reacted mixture is fed to a distillation system to produce a distillate comprising esters of organic acids and a residue comprising sterols and esters of steroid alcohols.

The residue (or part of it) is distilled again to produce a distillate comprising sterols.

Process 2

The reacted mixture is fed to a distillation system to produce a distillate comprising esters of organic acids and sterols and a residue comprising esters of steroid alcohols. The distillate (or part of it) is distilled again to produce a distillate and a residue comprising sterols.

Process 3

The reacted mixture is fed to a distillation system to produce a distillate and a residue comprising sterols and esters of steroid alcohols. The residue is crystallized as disclosed in Chilean Patent Application No. 2026/99, obtaining a crystallized fraction comprising sterols.

Process 4

The reacted mixture is crystallized as disclosed in Chilean Patent Application No. 2026/99, obtaining a crystallized fraction comprising sterols.

Short path distillation columns or molecular distillation columns with inner condensers, thin film evaporators with fractionation column and external condenser or combinations of said distillation systems, are considered suitable to carry out the above described distilling processes. Operating pressures of the columns ranges from 0.01 to 50 mbar; temperature of evaporating surfaces ranges from 120 to 400° C. and temperature of condensing surfaces ranges from 20 to 200° C.

Mixtures of a hydrocarbon, short chain aliphatic alcohol and water are suitable solvents for crystallizing the reacted mixture in processes 3 and 4.

Esters of steroid alcohols obtained by any of the processes 1, 2, 3 or 4 can be used as cholesterol lowering food ingredients. However, in order to increase the content of stanyl esters of the esters of steroid alcohols obtained by any of processes 1, 2, 3 or 4, these esters can be further saponified with sodium or potassium hydroxide in an alcoholic or aqueous solution giving rise to a saponified mixture comprising free steroid alcohols and fatty acid soaps and water or alcohol, or said esters of steroid alcohols can be enzymatically hydrolized with a suitable lipase, producing steroid alcohols and fatty acids. Components of the saponified mixture can be separated to produce fractions comprising fatty acid soaps and free steroid alcohols. The steroid alchols, once separated from the saponified or hydrolized mixtures, can be selectively transesterified to form a reacted mixture, which in turn can be fractionated if desired, by any of the processes 1, 2, 3 or 4.

Transesterification of steroid alcohols followed by separation of esters of steroid alcohols, hydrolysis or saponification of these esters and separation of steroid alcohols from the saponified or hydrolized mixture, further transesterification of the separated steroid alcohols, can be repeated as many times as needed, to get sterol free stanol esters or stanols.

Likewise, to increase the content of sterols of the steroid alcohols obtained from the reacted mixture, said alcohols, once separated from the reacted mixture by any of the processes 1, 2, 3 or 4 can be selectively transesterified and processed as described above to produce steroid alcohols with higher content of sterols. The complete process can be repeated as many times as needed to get stanol free steroid alcohols.

Transesterification reaction in the reacting mixture is carried out preferably in stirred reactors at reduced pressures, preferably at less than 300 mbar, and at temperatures ranging from 30 to 90° C., in the presence of a suitable amount of selective lipase, either free or immobilized.

Organic acids whose esters can be used in the transesterification reaction comprise fatty acids derived from edible oils such as rape oil, soy bean oil, cotton-seed oil, sunflower oil, palm oil, fish oils or may contain one or more fatty acids having from 2 to 14 carbon atoms per molecule. These fatty acids can be esterified with a short chain aliphatic alcohol such as methanol, ethanol, propanol or butanol in presence of sulfuric acid as catalyst as described in Example 1.

When it is desired to finalize the transesterifying reaction in the reacting mixture, the selective lipase is separated from the reacting mixture by filtration or centrifugation or by any suitable separation technics, giving rise to the reacted mixture.

According to what has been disclosed, a process for separating a fraction comprising sterols from a mixture comprising sterols and stanols comprises the steps of:

a) forming a reacting mixture by contacting a selective lipase with a reactant mixture comprising sterols and stanols and an ester selected from the group consisting of esters of an organic acids with a short chain aliphatic alcohol;

b) forming a reacted mixture by separating the selective lipase from the reacting mixture; and c) seprating from the reacted mixture a fraction comprising sterols.

Furthermore, a process for the selective transesterification of stanols in mixtures comprising sterols and stanols comprises forming a reacting mixture by contacting a selective lipase with a reactant mixture comprising sterols and stanols and an ester selected from the group consisting of esters of an organic acid a with a short chain aliphatic alcohol.

DETAILED DESCRIPTION OF THE DRAWINGS

DETAILED DESCRIPTION OF THE INVENTION

Figure 1:
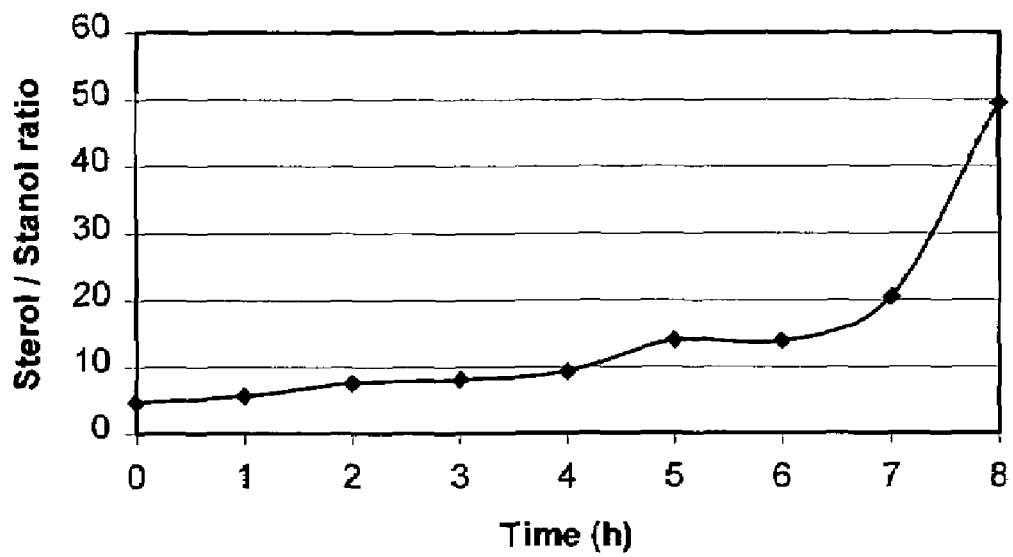
FIG. 1 is a chart which shows the variation of the mass ratio of sterols to stanols with time during reaction of Example 2.

The following examples illustrate ways of carrying out the present invention:

EXAMPLE 1

Preparation of Ethyl Ester of Sunflower Oil Fatty Acids 15.6 l technical grade ethanol, 313 g of concentrated sulfuric acid and 10.3 kg of commercial sunflower oil fatty acids were loaded under slight nitrogen flux into a 40 l stainless steel agitated reactor provided with electric calefaction, refrigeration coil, loading funnel, column, condenser, Dean-Stark separator, bottom valve, nitrogen injector and vacuum connection for distillation at reduced pressure. Nitrogen flux was interrupted and the mixture was refluxed at 77° C., for 10 hours with periodically monitoring the acid number. When the acid number reached 6.4, ethanol was distilled until 90% of the initial amount of ethanol was recovered. The mixture was cooled to 60° C. and diluted with 7 kg of hexane. Remaining acidity was neutralized with 8 kg of an aqueous solution of technical grade sodium carbonate at 10%. The aqueous phase was eliminated and the organic phase was washed three times with 1 kg of a water:ethanol mixture (1:1) to pH of 6.8. The neutral organic phase was desolventized at 95° C. and 25 mbar. Finally, 10.6 kg of ethyl esters of fatty acids of sunflower oil were obtained.

EXAMPLE 2

Transesterification of Wood Sterols with Immobilized Selective Lipase

A reacting mixture, whose initial composition can be seen in Table 2 below, was formed by mixing 1000 ml of ethyl esters of fatty acids of sunflower oil, 180 g of wood alcohol and 10 g of immobilized lipase of Alcaligenes sp. (MEITO SANGYO CO., LTD. Lipase-QLC) with lipolytic activity of 20,000 units per gram, were loaded into a 2000 ml SCHOTT-DURAN round bottom, flat flange reaction vessel with flat flange lid provided with 4 standard ground necks. The reactor was partially immersed in a water bath at 60° C. A reactor outlet was connected to a vacuum pump (TRIVAC B D 16B) maintaining the pressure of 2 mbar in the reactor during the reaction. Stirring was made by means of a magnetic stirrer. The agitation was stopped every hour allowing the settling of the immobilized lipase, and vacuum was broken in order to take a sample for analysis. The whole operation took less than a minute.

Analysis of free stanols and sterols was carried out using a Hewlett-Packard HP 6890 series 2 chromatograph provided with a HP-5 capillary column of 30 m long, 0.32 mm diameter and 0.25 mm film. Oven temperature was 300° C., injector and detector temperature was 320° C., carrier helium flux was 0.92 ml/min with 60:1 split and 15 minute program. The details of the analysis are disclosed in Chilean Patent Application No. 85/98.

Table 2 shows the variation of relative and absolute weight concentration of free stanols and sterols at the reaction time of Example 2

TABLE 2

Variation of the concentration (relative and absolute) of stanols and sterols with time of Example 2.

| | Reaction Time (h) | | | | | | | | |
|---|---|---|---|---|---|---|---|---|---|
| | 0 | 1 | 2 | 3 | 4 | 5 | 6 | 7 | 8 |
| Percentage of sterols and stanols in the reacting mixture | | | | | | | | | |
| campesterol | 1.25 | 1.24 | 1.10 | 1.07 | 1.06 | 1.12 | 1.14 | 1.06 | 1.04 |
| campestanol | 0.14 | 0.07 | 0.00 | 0.00 | 0.00 | 0.00 | 0.00 | 0.00 | 0.00 |
| sitosterol | 11.60 | 11.82 | 11.07 | 10.64 | 10.57 | 10.53 | 10.31 | 9.98 | 10.04 |
| sitostanol | 2.58 | 2.23 | 1.59 | 1.45 | 1.25 | 0.83 | 0.82 | 0.54 | 0.22 |
| Total | 15.57 | 15.36 | 13.76 | 13.17 | 12.89 | 12.48 | 12.28 | 11.58 | 11.30 |
| Relative percentage of free sterols and stanols in the reacting mixture | | | | | | | | | |
| campesterol | 8.01 | 8.10 | 7.98 | 8.15 | 8.25 | 9.00 | 9.27 | 9.17 | 9.23 |
| campestanol | 0.92 | 0.47 | 0.00 | 0.00 | 0.00 | 0.00 | 0.00 | 0.00 | 0.00 |
| sitosterol | 74.48 | 76.93 | 80.43 | 80.82 | 82.05 | 84.35 | 84.02 | 86.17 | 88.79 |
| sitostanol | 16.59 | 14.50 | 11.59 | 11.03 | 9.70 | 6.65 | 6.72 | 4.65 | 1.98 |

FIG. 1 shows the variation of the mass ratio of sterols to stanols with time during the reaction of Example 2.

Figure 2:
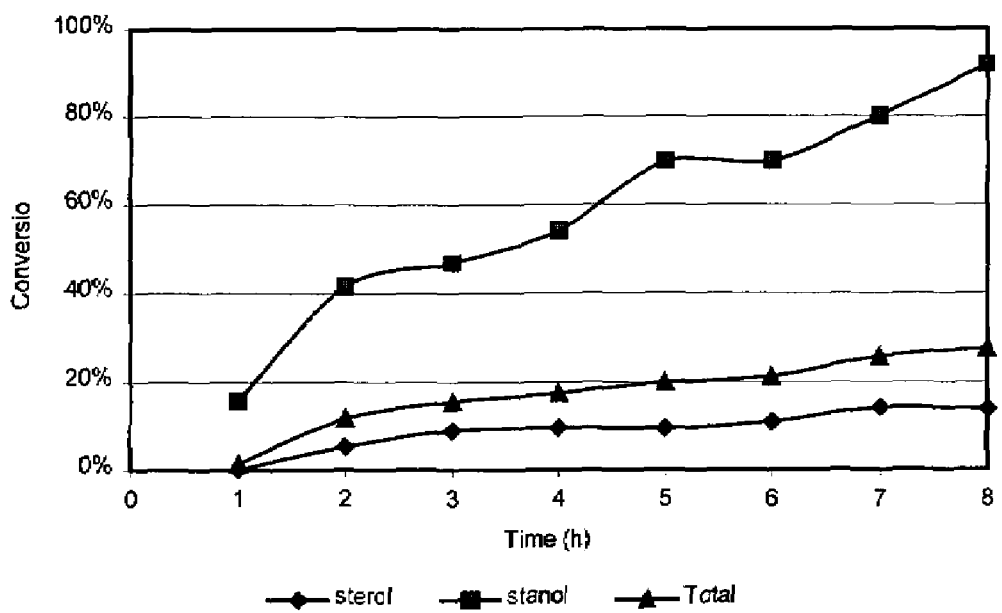
FIG. 2 is a chart which shows the variation of the conversion of sterols and stanols to esters with time during the reaction of Example 2.

FIG. 2 shows the variation of the conversion of sterols and stanols to esters with time during the reaction of Example 2.

During the reaction, mass ratio of sterols to stanols increased more than 12 times. Conversion of stanols was nearly 100%, while conversion of sterols was scarcely 20%; this fact demonstrates a surprising and unexpected selectivity of the lipase toward the transesterification of stanols, allowing to obtention of a practically stanol-free mixture of sterols. It can also be observed that campesterol, whose initial concentration was lower than half of the initial concentration of stanols, remains practically intact during the reaction, which confirms the surprising selectivity of the lipase utilized.

EXAMPLE 3

Transesterification of Wood Sterols with Free Lipase

A reacting mixture of the composition shown in Table 3 below, was formed by mixing 854 g of esters of fatty acids of sunflower oil, 141 g of wood sterols and 16 g of free selective lipase of Alcaligenes sp. (MEITO SANGYO Co. Ltd., Lipase-QL) with activity of 30,000 units per gram, were loaded into the reactor of Example 2. Temperature and pressure in the reactor were 60° C. and 2 mbar respectively. Samples were taken at intervals, centrifuged at 60° C. and 10,000 rpm for 15 minutes to separate the lipase dispersed in the sample. Results are shown in Table 3. As can be observed by comparing the data of Tables 2 and 3, there are no significant differences in conversion between immobilized and free lipase.

TABLE 3

Variation of the concentration (relative and absolute) of stanols and sterols with time of Example 3.

| | Reaction Time (h) | | | | | | | |
|---|---|---|---|---|---|---|---|---|
| | 0 | 1 | 2 | 3 | 4 | 5 | 6 | 7 |
| Percentage of sterols and stanols in the reacting mixture | | | | | | | | |
| campesterol | 1.09 | 0.92 | 0.83 | 0.79 | 0.79 | 0.78 | 0.79 | 0.75 |
| campestanol | 0.12 | 0.04 | 0.00 | 0.00 | 0.00 | 0.00 | 0.00 | 0.00 |
| sitosterol | 10.02 | 8.51 | 8.28 | 7.63 | 7.83 | 7.65 | 7.42 | 7.30 |
| sitostanol | 1.88 | 0.98 | 0.76 | 0.58 | 0.50 | 0.43 | 0.38 | 0.32 |
| Total | 13.12 | 10.45 | 9.87 | 8.99 | 9.11 | 8.85 | 8.60 | 8.38 |
| Relative Percentage of free sterols and stanols in the reacting mixture | | | | | | | | |
| campesterol | 8.32 | 8.76 | 8.44 | 8.75 | 8.65 | 8.80 | 9.20 | 9.01 |
| campestanol | 0.88 | 0.39 | 0.00 | 0.00 | 0.00 | 0.00 | 0.00 | 0.00 |
| sitosterol | 76.42 | 81.48 | 83.83 | 84.81 | 85.87 | 86.36 | 86.33 | 87.19 |
| sitostanol | 14.37 | 9.37 | 7.73 | 6.44 | 5.48 | 4.84 | 4.46 | 3.80 |

EXAMPLE 4

Enzymatic Transesterification of Sterols with Ethyl Acetate

A reactive mixture was formed by mixing 300 g of ethyl acetate (Mallinckrodt AR 4992) with 0.01% humidity, 100.3 g of wood alcohols and 6 g of immobilized selective lipase Alcaligenes sp (MEITO SANGYO Co. Ltd. Lipase-QLC), were loaded into a 2-l round bottom flat flange reaction vessel with flat flange lid provided with 5 standard ground necks, cylindrical graduated dropping funnel with pressure equalization tube and a Dean-Stack distillation head connected to a condenser and a glass flask for receiving distillates.

The reactor was partially immersed in a thermostated bath at 60°. Stirring was made by means of a magnetic stirrer. Pressure in the reactor was 200 mbar. Fresh ethyl acetate was fed from the dropping funnel at the rate of distillate recovery After 4 hours of reaction, the reacted mixture was recovered and filtered. The filtered reacted mixture was desolventized and 101.1 g of residue was recovered. The residue was analyzed using gas chromatography. Conversion of sterols was 3.1% and that of stanols was 45.9%.

EXAMPLE 5

Fractionating a Reacted Mixture 950 g of reacted mixture produced as described in example 2, was fed at the rate of 1.7 g/min into a UIC KDL-4 short path distillation column. Temperature of the evaporating surface was 180° C. Temperature of the inner condenser was 30° C. and the pressure in the column was 10 mbar. A distillate fraction free of sterols and stanols comprising ethyl esters of sunflower fatty acids by the amount of 773 g was collected from the column at the inner condenser and a separate 171 g residue fraction was collected at the bottom of the column.

165 g of residue was the fed at the rate 1.5 g/min to the UIC KDL-4 short path column utilized as a thin film evaporator, (without inner condenser), connecting the distillate or vapor outlet of the column to a packed bed (8 mm Poropak stainless steel berl saddles packing) fractionating column with overhead condenser. Evaporating surface of the thin film column was maintained at 250° C. and temperature of external condenser was 150° C. Operating pressure was 0.1 mbar. 155 g of a distillate fraction comprising 96% of total steroid alcohols, and containing 50 times as much sterols as stanols was collected at the overhead condenser, and 7 g of a residue fraction at the bottom of the KDL-4 column was collected containing less than 1% of free steroid alcohols.

EXAMPLE 6

Fractionating a Reacted Mixture 920 g of reacted mixture produced as described in example 3, was fed at the rate of 1.5 g/min to the UIC KDL-4 short path distillation column. Evaporating surface was maintained at the temperature of 180° C. and internal condenser at the temperature of 30° C. Pressure in the column was 10 mbar. A distillate fraction free of sterols and stanols comprising ethyl esters of sunflower fatty acids by the amount of 771 g was collected from the column at the inner condenser and a separate 145 g residue fraction was collected at the bottom of the column.

140 g of the residue, 400 g of hexane, 20 g of ethanol and 20 g of water were loaded intoto a 1-l glass flask and refluxed until dissolution. After cooling the solution to 5° C. and letting stand to allow the formation of crystals, filtering and drying, 130 g of crystals comprising 86% of steroid alcohols containig 25 times as much sterols as stanols were recovered.

EXAMPLE 7

Saponification of the Residue of a Thin Film Evaporator 5 g of the residue of the thin film evaporator obtained in Example 5, and 20 ml of alcoholic solution of sodium hydroxide at 8% were loaded into a 100 ml Erlenmeyer glass flask. The mixture was refluxed for 1 hour. Then, 20 ml of distillated water was added and the mixture was extracted four times with 50 ml portions of hexane.

The hexanic phase was washed to neutral pH with 10 ml portions of a mixture of water:ethanol (1:1) and was desolventized in a rotavapor. 2.5 g of a desolventized residue comprising 97% steroid alcohols (58% stanols, 42% sterols) was obtained.

EXAMPLE 8

Reesterification 30 l of methyl esters of fatty acids of raps oil (Härting S. A.), 5000 g of wood alcohols, whose relative composition is shown in Table 4, and 250 g of immobilized lipase of Alcaligenes sp (MEITO SANGYO Co. Ltd. Lipase-QLC) with a lipolytic activity of 20,000 units per gram, were loaded into a 40-l stainless steel agitated reactor provided with electric heating, refrigeration coil, loading funnel, column, condenser, Dean-Stack separator, bottom valve, nitrogen injector and vacuum connection for distillation at reduced pressure.

The mixture was heated at 60° C. under constant agitation at 300 rpm at reduced pressure of 20 mbar for 10 hours. The reacting mixture was filtered using a 50-micron polyester bag and 31.75 kg of a reacted mixture was recovered. The filtered enzyme was washed with hexane, and dried.

The reacted mixture was fed at the rate of 12 g/min to the UIC KDL-4 short path distillation column. In this case the column was utilized as thin film evaporator, and the distillates from the evaporating surface of the column were led to an external packed bed column (8 mm Poropak stainless steel berl saddles packing) with overhead condenser. Evaporating surface tempeature was 200° C. and temperature of packed column top condenser was 30° C. The pressure in the KDL-4 column was 5 mbar. 23.15 kg of a distillate fraction at the overhead condenser and 7.40 kg of a residue fraction at the bottom of the KDL-4 column were recovered.

The residue was fed again to the thin film evaporator assembly as described above. The temperature of the evaporating surface was maintained at 250° C. and temperature of overhead condenser was 150° C. Operating pressure was 0.1 mbar. 5.23 kg of a distillate fraction at the overhead condenser, and 2.07 kg of a residue fraction from the bottom of the KDL-4 column were collected. Chromatographic analysis of said residue fraction did not detect sterols or stanols.

2.0 kg of the residue was charged into the 40-l stainless steel agitated reactor and 3 l of ethanolic solution of sodium hydroxide at 8% was added. The mixture was refluxed for 2 hours and cooled to 25° C. adding 3 l of water, and the resulting mixture was extracted four times with 10-l portions of hexane. The hexanic phase was washed to neutral pH and then partially desolventized in the same reactor. The hexanic concentrate was finally desolventized in a rotovapor at reduced pressure. 1070 g of a desolventized residue (Residue 3, table 4), whose composition is shown in Table 4, was collected.

4.00 kg of distillate of the first distillation, 800 g of the desolventized residue and 40 g of the immobilized lipase recovered in the present example were charged into a 6-l SCHOTT-DURAN reactor. The reactor was partially immersed in a thermostated bath at 60° C.

The mixture was kept under agitation at reduced pressure of 20 mbar for 2 hours then filtered through a 50-micron polyester bag. 4.75 kg of reacted mixture was recovered. The filtered enzyme was washed with hexane, and dried.

2.00 kg of the reacted mixture was fed at the rate of 2 g/min to the UIC KDL-4 short path column with the evaporating surface kept at the temperature of 180° C. and inner condenser at the temperature of 30° C. Pressure of the column was 10 mbar. 1541 g of a distillate fraction and 432 g of a residue was recovered from the column.

420 g of the said residue was fed at the rate of 1.5 g/min to the to the falling film evaporator assembly as described above. The temperature of the evaporating surface was maintained at 250° C. and temperature of the overhead condenser was 150° C. Pressure was 0.1 mbar. 294 g of distillate fraction at the condenser and 109 g of a residue-fraction at the bottom of the column were collected.

100 g of the latter residue was fed at the rate of 1.5 g/min to the UIC KDL-4 short path distillation column, with the evaporating surface kept at the temperature of 250° C. and condenser temperature at 100° C. Pressure in the column was 0.1 mbar. 96 g of fifth distillate fraction at the inner condenser and 3 g of a residue fraction (Residue 7 in Table 4) at the bottom of the column were collected.

2 g of the latter distillate fraction was saponified as described in Example 7. 1 g of desolventized hexanic extract, whose composition is shown in Table 4, was collected

TABLE 4

Content of steroid alcohols of Example 8.

| | Relative composition | | | | |
|---|---|---|---|---|---|
| | Campesterol | Campestanol | Sitosterol | Sitostanol | Purity |
| Wood alcohols | 8.24 | 0.92 | 76.39 | 13.21 | 94.2 |
| Residue 3 | 4.81 | 3.33 | 41.47 | 50.39 | 96.0 |
| Residue 7 | 0.98 | 5.56 | 9.29 | 84.17 | 95.1 |

What is claimed is:

1. A process of transesterifying a mixture of stanols and sterols comprising,
   a. reacting the mixture with an ester of a fatty acid in the presence of a microbial lipase to form a reacting mixture; and
   b. separating the microbial lipase from the reacting mixture to form a reacted mixture;
   wherein the lipase is derived from *Alcaligenes* sp.,
   wherein the conversion of stanols to fatty stanyl esters is higher than the conversion of sterols to fatty steryl esters, and
   wherein the ester of the fatty acid is a methyl or ethyl ester.

2. The process according to claim 1, wherein the fatty acid contains from 2 to 25 carbon atoms.

3. The process according to claim 1, wherein the reaction temperature is from 30° C. to 90° C. and the reaction pressure is less than 300 mbar.

4. A process for separating a first blend of stanols and sterols from a first mixture, the process comprising:
   a. reacting the first mixture with an ester of a fatty acid in the presence of a lipase of *Alcaligenes* sp. to form a reacting mixture;
   b. separating the lipase from the reacting mixture to form a reacted mixture; and
   c. distilling the reacted mixture to form a distillate consisting essentially of a second blend of stanols and sterols,
   wherein the mass ratio of stanols to sterols in the second blend is less than the mass ratio of stanols to sterols in the first mixture.

5. The process according to claim 4, wherein the reaction temperature is from 30° C. to 90° C. and the reaction pressure is less than 300 mbar.

6. The process according to claims 4, wherein the fatty acid contains from 2 to 25 carbon atoms.

7. The process according claim 4, wherein distillation occurs at a pressure of 10 mbar and a temperature of 180° C. to give a first distillate and a first residue wherein the fatty acids are obtained from sunflower oil.

8. The process according to claim 7, wherein the first residue is distilled at a pressure of 0.1 mbar and a temperature of 250° C. to give a second distillate and a second residue wherein the fatty acids are obtained from sunflower oil.

9. The process according to claim 8, wherein the second distillate consists essentially of free sterols.

10. The process according to claim 8, wherein the second residue consists essentially of fatty acid esters of sterols and stanols.

* * * * *